(12) United States Patent
Moisan et al.

(10) Patent No.: US 8,101,748 B2
(45) Date of Patent: Jan. 24, 2012

(54) **FLUORINATED CATHARANTHINE DERIVATIVES, THEIR PREPARATION AND THEIR UTILISATION AS *VINCA* DIMERIC ALKALOID PRECURSORS**

(75) Inventors: Lionel Moisan, Gif sur Yvette (FR); Sébastien Comesse, Le Havre (FR); Emerson Giovanelli, Laxou (FR); Bernard Rousseau, Levallois-Perret (FR); Eric Doris, Orsay (FR); Paul Hellier, Castelnau de Montmiral (FR)

(73) Assignees: Pierre Fabre Medicament, Boulogne-Billancourt (FR); Commissariat a l'Energie Atomique, Paris (FR)

( * ) Notice: Subject to any disclaimer, the term of this patent is extended or adjusted under 35 U.S.C. 154(b) by 392 days.

(21) Appl. No.: 12/442,193

(22) PCT Filed: Sep. 20, 2007

(86) PCT No.: PCT/EP2007/059991
§ 371 (c)(1),
(2), (4) Date: Mar. 20, 2009

(87) PCT Pub. No.: WO2008/034882
PCT Pub. Date: Mar. 27, 2008

(65) Prior Publication Data
US 2010/0093997 A1    Apr. 15, 2010

Related U.S. Application Data

(60) Provisional application No. 60/826,245, filed on Sep. 20, 2006.

(30) Foreign Application Priority Data

Sep. 20, 2006 (FR) .................................... 06 08226

(51) Int. Cl.
*C07D 223/14* (2006.01)
(52) U.S. Cl. ....................................................... 540/579
(58) Field of Classification Search .................. None
See application file for complete search history.

(56) References Cited

FOREIGN PATENT DOCUMENTS
WO    WO-95/03312 A1    2/1995
WO    WO-98/45301 A1    10/1998

OTHER PUBLICATIONS

Duflos, Alain, et al. "Novel Aspects of Natural and Modified Vinca Alkaloids" Current Med. Chem.-Anti-Cancer Agents, 2002, vol. 2, No. 1, pp. 1-16.

Fahy, Jacques, et al. "Vinflunine: Discovery and Synthesis of a Novel Microtubule Inhibitor", Seminars in Oncology, vol. 35, No. 2, Suppl. 3, Jun. 2008, pp. S3-S5.
Andriamialisoa, R.Z., et al., "Composes Antitumoraux Du Groupe De La Vinblastine: Nouvelle Methode De Preparation" Tetrahedron, 1980, vol. 36, pp. 3053-3060.
Jacquesy, J., et al., "Fluorination in superacids: a novel access to biologically active compounds" Journal of Fluorine Chemistry vol. 114, No. 2, (2002), pp. 139-141. XP-004351167.
Guéritte, F., et al., "The Vinca Alkaloids", Anticancer Agents from Natural Products, May 13, 2005, pp. 123-135.
Fahy, J., et al. "Vinca Alkaloids in Superacidic Media: A Method for Creating a New Family of Antitumor Derivatives", Journal of the American Chemical Society, vol. 119, No. 36, 1997, pp. 8576-8577. XP-00207072890.
Fahy, J., et al., "Vinca Alkaloids in Superacidic Media: a Method for Creating a New Family of Antitumor Derivatives", Seminars of Oncology, vol. 35, Supp. 2 (2008) Revised, pp. S1-S5.
Jacquesy, J., "Reactivity of Vinca alkaloids in superacid An access to vinflunine, a novel anticancer agent" Journal of Fluorine Chemistry, vol. 127, No. 11, Sep. 16, 2006, pp. 1484-1487. XP-005767837.

*Primary Examiner* — Noble Jarrell
(74) *Attorney, Agent, or Firm* — Birch, Stewart, Kolasch & Birch, LLP.

(57) ABSTRACT

The fluorinated derivatives of catharanthine according to the invention respond to the general formula I:

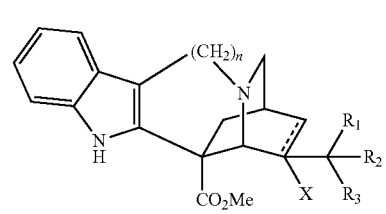

in which:
the dotted line expresses the possibility of the presence of a double bond when the substitution —X is absent or else a single bond when —X designates a substitution for a group:
H,
OR,
NR'R",
SR, or
a halogen atom with R, R' and R" designating independently of one another a hydrogen atom or a linear or branched alkyl group in $C_1$ to $C_6$,
$R_1$, $R_2$ and $R_3$ represent independently of one another an atom of hydrogen, of fluorine or a methylated group, on the condition nevertheless that at least one of the radicals $R_1$ and $R_2$ represents an atom of fluorine, and
n=1 or 2.

26 Claims, No Drawings

FLUORINATED CATHARANTHINE DERIVATIVES, THEIR PREPARATION AND THEIR UTILISATION AS *VINCA* DIMERIC ALKALOID PRECURSORS

This application is the National Phase of PCT/EP2007/059991 filed on Sep. 20, 2007, which claims priority under 35 U.S.C. 119(e) to U.S. Provisional Application No. 60/826,245 filed on Sep. 20, 2006, and under 35 U.S.C. 119(a) to Patent Application No. 06/08226 filed in France on Sep. 20, 2006, respectively, all of which are hereby expressly incorporated by reference into the present application.

The present invention relates to fluorinated derivatives of catharanthine, their preparation and their use as a precursor of fluorinated dimeric *Vinca* alkaloids, and vinflunine in particular.

Vinflunine 1 is a wide-spectrum anticancer agent developed by Pierre Fabre laboratories. This molecule is a fluorinated analogue of vinorelbine 5 (Navelbine®) which is the reference drug for treatment of breast and lung cancer. The structure of vinflunine is very similar to that of vinorelbine, from which it differs only by the presence of a group gem-difluorinated in $C_{20'}$, and by the absence of the double bond $C_{3'}$-$C_{4'}$. Vinflunine 1 (Javlor®) is the most active fluorinated compound discovered over recent years. It is currently in phase III of clinical trials in the treatment of breast, bladder and lung cancer, and is heralded today as the most promising molecule to have originated from the family of *Vinca* alkaloids.

Vinflunine may be prepared from 3',4'-anhydrovinblastine 4 precursor which is obtained by the coupling of two sub-units catharanthine 2 and vindoline 3, which are extracted directly from the leaves of the Madagascar periwinkle (Diagram 1). Alternatively vinflunine may be prepared by direct fluorination of vinorelbine.

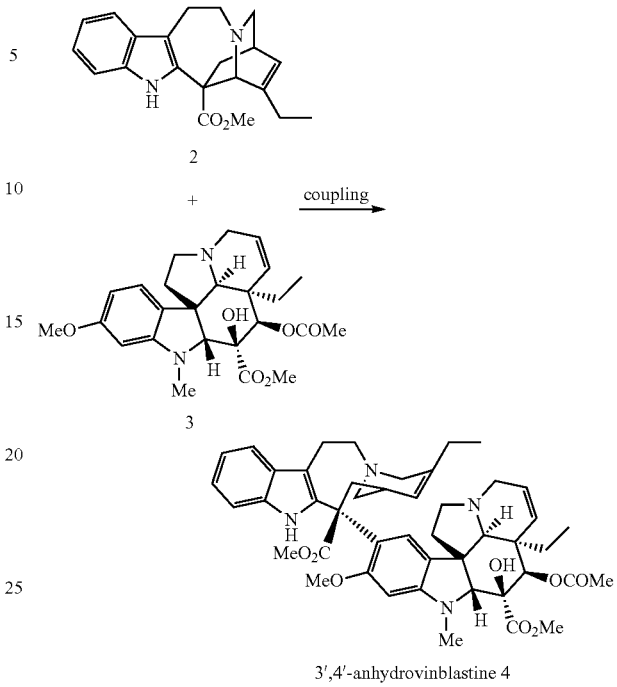

Diagram 1

3',4'-anhydrovinblastine 4

3',4'-Anhydrovinblastine 4 can then be transformed into vinorelbine 5 by ring contraction, or into vinflunine 1 by introduction of two fluorine atoms on the lateral chain of the "north" fragment followed by ring contraction (Diagram 2). This fluorination operation takes place in a superacid medium (HF—SbF$_5$) in the presence of a chlorinated solvent. These reaction conditions are particularly drastic, resulting in partial degradation of the dimeric alkaloid 4 and thus in a drop in the overall chemical yield of the transformation. The gem-difluorination in $C_{20'}$ proceeds with concomitant reduction of the $C_{3'}$-$C_{4'}$ double bond. The stereocentre formed at 4' has an absolute configuration (R). Vinflunine can also be prepared by fluorination of vinorelbine 5 (Navelbine®). The synthesis thereof is carried out by ring contraction of 3',4'-anhydrovinblastine 4.

Diagram 2

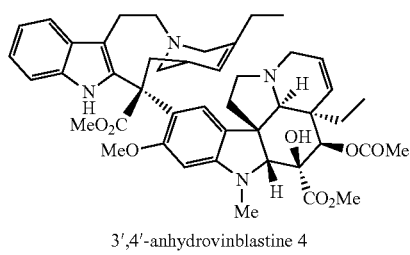

3',4'-anhydrovinblastine 4

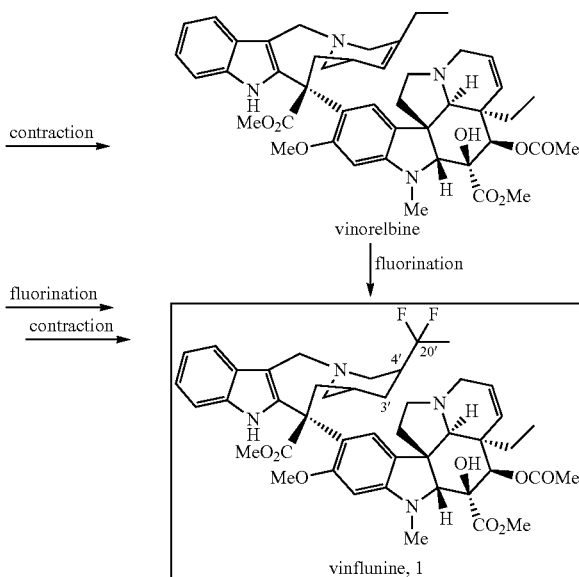

vinorelbine vinflunine, 1

3',4'-Anhydrovinblastine 4 is a product with high added. The fluorination stage thus causes the sacrifice of a considerable quantity of this precious intermediate. This situation risks resulting at times in a strong increase in the demand for periwinkle leaves. Several strategies are being studied for continuing the development of vinflunine 1.

Based on the observation that the fluorination of 3',4'-anhydrovinblastine in a superacid mixture modifies only its "north" fragment which originates from catharanthine, a solution consisting of introducing fluorine atoms directly to the skeleton of catharanthine 2 has been advocated, within the scope of the present invention. This approach has a number of advantages: it introduces fluorine upstream in the synthesis to a product with lesser added value than 3',4'-anhydrovinblastine 4. The synthesis of vinflunine could then be accessed via a biomimetic coupling with vindoline 3. In fact, 20',20'-difluorocatharanthine 6 can then be coupled to vindoline 3 to obtain 3',4'-anhydro-20',20'-difluorovinblastine 7. The latter is finally converted into vinflunine 1, in a process familiar to the specialist, by ring contraction reaction followed by reduction of the non-saturated $C_{3'}$-$C_4$ double bond. (Diagram 3).

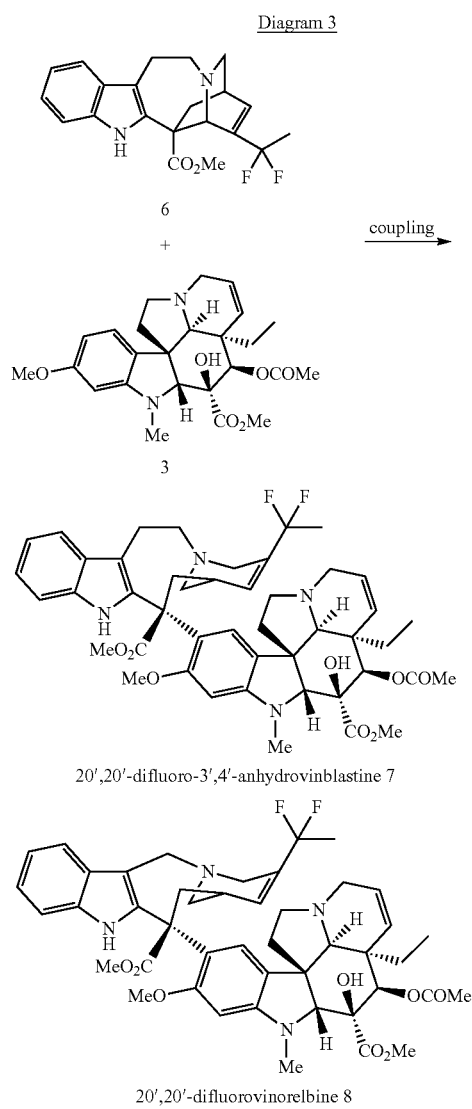

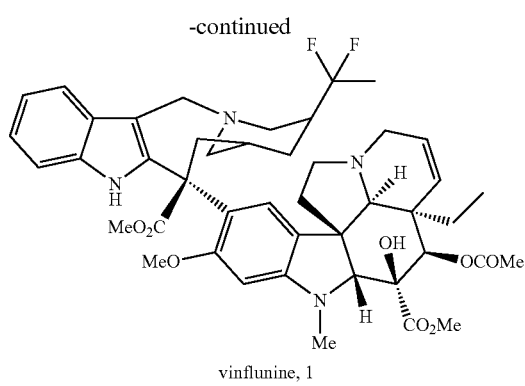

vinflunine, 1

This approach also allows access to other original difluorinated derivatives (3',4'-anhydro-20',20'-difluorovinblastine 7, 20',20'-difluorovinorelbine 8) which are not accessible under conventional superacid conditions. These molecules are all the more interesting since study of the structure activity relation has shown that the region 4' and 20' of the *Vinca* alkaloids is strongly associated with their anti-tumoral activity. Also, the coupling of synthesis intermediates (and derivatives) of fluorinated catharanthine likewise produces other original fluorinated derivatives of dimeric alkaloids of *Vinca*.

Therefore, the present invention relates to fluorinated derivatives of catharanthine responding to the general formula I:

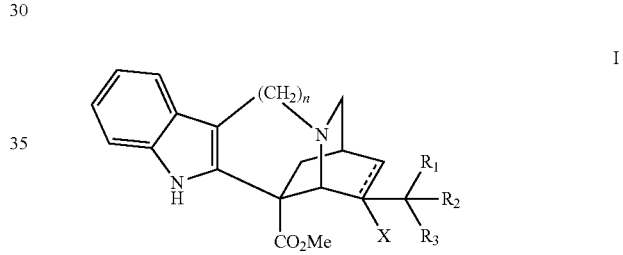

in which:
the dotted line expresses the possibility of the presence of a double bond when the substitution —X is absent or else of a single bond when —X designates a substitution for a group:
H,
OR,
NR'R",
SR, or
an atom of halogen with R, R' and R" designating independently of one another an atom of hydrogen or a linear or branched alkyl group in $C_1$ to $C_6$,
$R_1$, $R_2$ and $R_3$ represent independently of one another an atom of hydrogen, fluorine or a methylated group, on the condition all the same that at least one of the radicals $R_1$ and $R_2$ represents an atom of fluorine, and
n=1 or 2.

The present invention likewise relates to the utilisation of these fluorinated derivatives as synthesis intermediates useful for the preparation of fluorinated dimeric alkaloids of *Vinca*, in particular as reactive partners in coupling reactions with vindoline or with a derivative of vindoline. In particular, vinflunine will be obtained by coupling vindoline and 20,20-20,20-difluorocatharanthine, resulting in 20',20'-difluoro-3',4'-anhydrovinblastine which, in turn, will be subjected to a ring contraction reaction followed by reduction reaction of the endocyclic double bond at position $C_{3'}$-$C_{4'}$.

Introduction of the fluorine atoms to catharanthine 2 could be envisaged via oxidation of the lateral chain of catharanthine and fluorination.

Diagram 4

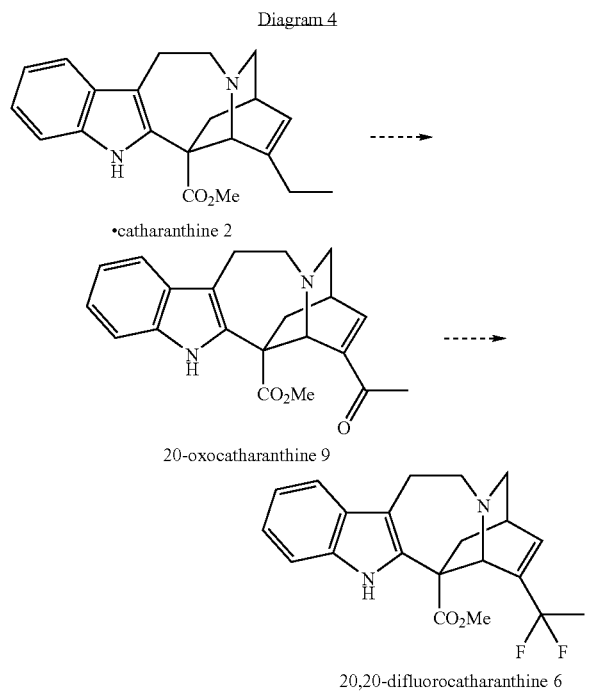

•catharanthine 2

20-oxocatharanthine 9

20,20-difluorocatharanthine 6

The preparation of the fluorinated catharanthine derivatives of the invention implies thus an oxidation step of the lateral chain of catharanthine, which is carried out in conditions leading to an oxidised derivative of catharanthine responding to the general formula II:

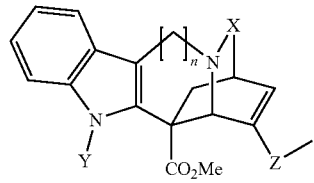

II in which:
n=1 or 2,
X designates a C=O or C=S group,
Y designates a $CO_2R$, $SO_2R$ or COR group with R designating an aryl group or a linear or branched alkyl group in $C_1$ to $C_4$, and
Z designates a CH—OH or C=O group.

Therefore, the present invention relates also to oxidised derivatives of catharanthine responding to the general formula II:

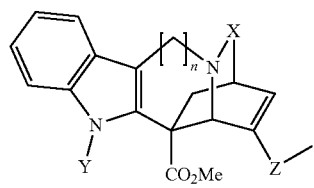

II in which:
n=1 or 2,
X designates a C=O or C=S group,
Y designates a $CO_2R$, $SO_2R$ or COR group with R designating an aryl group or a linear or branched alkyl group in $C_1$ to $C_4$, and
Z designates a CH—OH or C=O group.

A preferred oxidised derivative of catharanthine according to the formula II is a derivative wherein:
n=2,
X designates a C=O group,
Y designates a $CO_2R$ group with R designating a linear or branched alkyl group in $C_1$ to $C_4$, and
Z designates a CH—OH or C=O group.

The present invention likewise relates to the use of these oxidised derivatives as synthesis intermediates useful for the preparation of fluorinated dimeric alkaloids of *Vinca*, in particular vinflunine. This preparation implies a fluorination of the oxidised derivative of catharanthine followed by deprotection of the two nitrogen atoms, resulting in a fluorinated derivative of catharanthine of the invention. The preparation further implies a coupling reaction between the said fluorinated derivative and vindoline or a derivative of vindoline. In particular, vinflunine will be obtained by coupling vindoline and 20,20-difluoro-catharanthine, obtained by fluorination and deprotection of the two nitrogen atoms of an oxidised derivative of catharanthine as defined above for which n=2, X=C=O, Y=$CO_2R$ with R as defined above and Z=C=O, resulting in 20',20'-difluoro-3',4'-anhydrovinblastine which, in turn, will be subjected to a ring contraction reaction followed by a reduction reaction of the endocyclic double bond at position $C_{3'}$-$C_{4'}$.

The term "aryl" refers herein to a cyclic aromatic group of from 5 to 7 carbon atoms, comprising optionally a heteroatom, in particular an oxygen or a nitrogen, such as, for example, a phenyl or a pyridinyl group.

Thus, as an example, 20,20-difluorocatharanthine can be synthesised as follows.

Activation of the lateral chain can be achieved by isomerisation of the endocyclic double bond to the exocyclic position prior to further functionalisation. The isomeration reaction of 2 in 10 is performed under partial hydrogen pressure in the presence of palladium on carbon. The indole ring is then protected in the form of methyl carbamate 11 and tertiary nitrogen in the form of amide 12.

Diagram 5

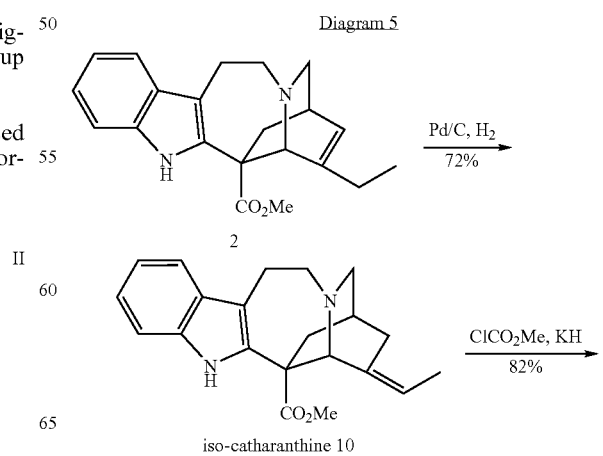

iso-catharanthine 10

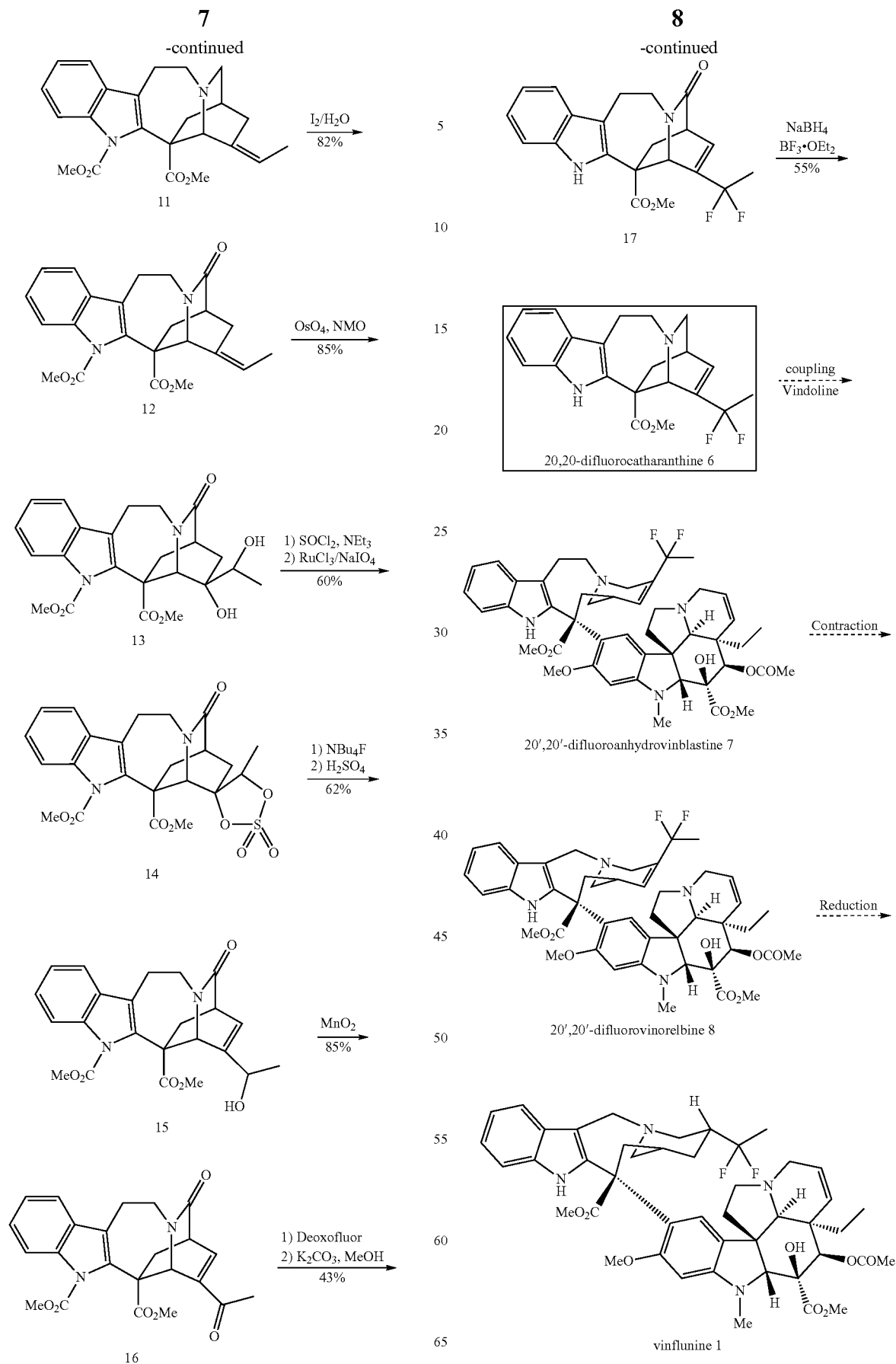

The double bond of 12 is then dihydroxylated by $OsO_4$ and the resulting diol 13 is activated twice in the form of cyclic sulphate 14. The allylic alcohol 15 is obtained by action of tetrabutyl ammonium fluoride, followed by treatment with sulphuric acid. The alcohol function is then oxidised by $MnO_2$ and the resulting enone 16 is difluorinated by action of Deoxofluor™ (bis(2-methoxyethyl)aminosulfide trifluoride). The protective group of indole (carbamate) is eliminated by the action of potassium carbonate in methanol. The amide group of 17 is finally reduced to result in 20,20-difluorocatharanthine 6. The latter can, in the same way as catharanthine of natural origin, be coupled to vindoline to provide the fluorinated analogue of 3',4'-anhydrovinblastine (7) which, after ring contraction, results in the fluorinated analogue of vinorelbine (8). Finally, selective reduction of the double bond of the north fragment results in the formation of vinflunine 1.

According to a variant synthesis route, the allylic alcohol 15 can also be obtained by an initial protection of the indole ring of catharanthine 2 by a methyl carbamate (compound 26) and of tertiary nitrogen in the form of amide 27. The latter can then be oxidised directly in allylic alcohol 15 by $SeO_2$ (Diagram 6).

The synthesis intermediates to 20,20-difluorocatharanthine 6 can be exploited by functional arrangements which do not result in 20,20-difluorocatharanthine but in structural analogues. These analogues can, in the same way as catharanthine of natural origin, be coupled to vindoline to result in the corresponding fluorinated dimeric alkaloids.

Accordingly, starting from the intermediate 13 oxidation of the secondary alcohol function gives access to ketone 18. Fluorination of the ketoalcohol 18 by DAST (diethylaminosulphide trifluoride) generates difluoro-alcohol 19. The latter could, after the usual stages of deprotection (→20) be coupled to vindoline to form the difluorinated analogue 21 of vinblastine which is likewise an alkaloid having notable anti-cancer properties (Diagram 7).

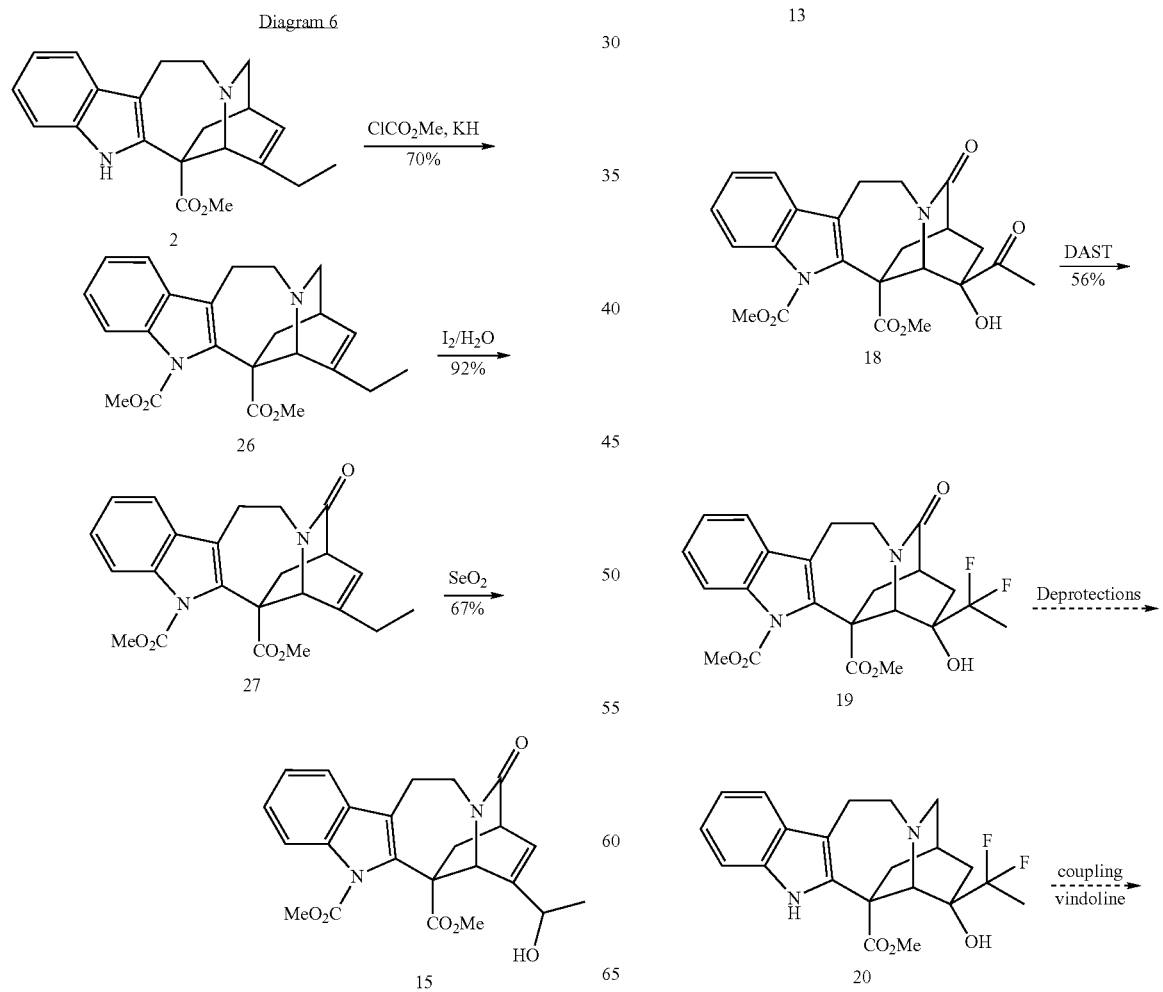

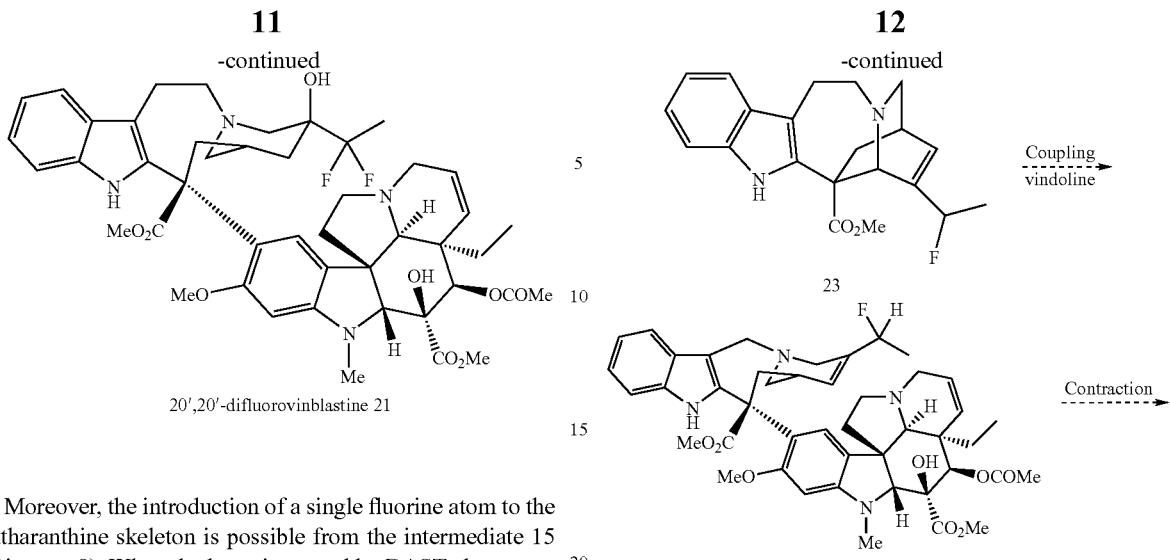

Moreover, the introduction of a single fluorine atom to the catharanthine skeleton is possible from the intermediate 15 (Diagram 8). When the latter is treated by DAST, the monofluorinated product of the lateral chain (22) is formed. As already mentioned hereinabove, this product results in the mono fluoro analogues 3',4'-anhydro-20'-fluorovinblastine 24 and 20'-fluorovinorelbine 25 which can lead to the monofluorinated analogue of vinflunine by an additional stage of reduction of the double bond.

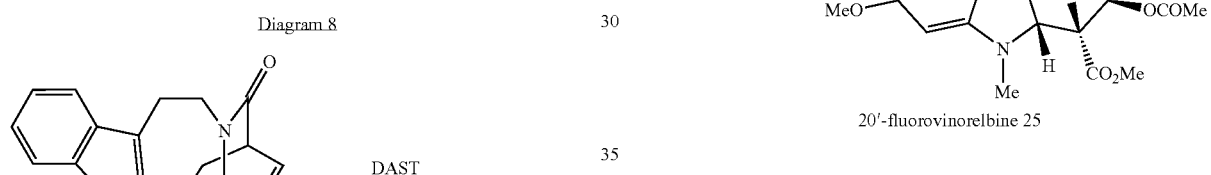

Finally, isocatharanthine 10 can also be used as a synthesis intermediate in the preparation of fluorinated dimeric alkaloids of *Vinca*, and in particular vinflunine. This preparation implies a coupling reaction between the said isocathranthine and vindoline or a derivative of vindoline.

Thus, vinflunine 1 can be obtained by coupling vindoline 3 and isocatharanthine, resulting in 4',20'-anhydrovinblastine 28. This intermediate can then be difluorinated using the conditions described for the fluorination of 3',4'-anhydrovinblastine 4 (J.-C. Jacquesy et al., *Journal of Fluorine Chemistry*, 2002, 114, 139). The obtained product, (4'R)-4'-deoxy-20',20'-difluorovinblastine 30, is identical to the product formed by fluorination of 3',4'-anhydrovinblastine 4. Transformation of 30 in vinflunine by ring contraction is described in literature (J.-C. Jacquesy et al., *Journal of Fluorine Chemistry*, 2002, 114, 139) (Diagram 9).

Alternately, vinflunine 1 can be also obtained by ring contraction of 4',20'-anhydrovinblastine 28, resulting in 29, followed by a gem difluorination according to the same methods as described above.

Diagram 9

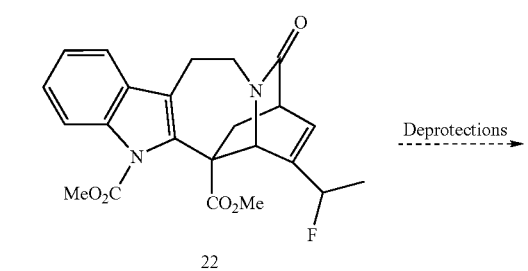

-continued

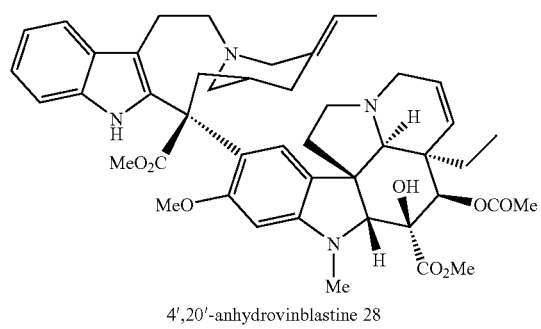

4',20'-anhydrovinblastine 28

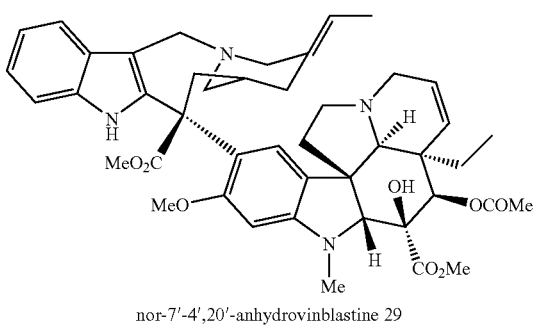

nor-7'-4',20'-anhydrovinblastine 29

| superacid medium

| superacid medium

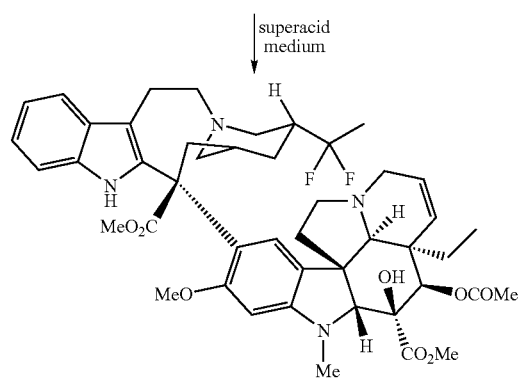

(4'R)-4'-deoxy-20',20'-difluorovinblastine 30 contraction →

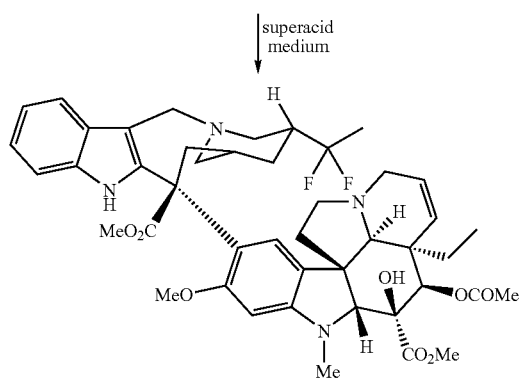

vinflunine 1

It appears that the present invention offers an alternative strategy to the classic synthesis of vinflunine, allowing the use of a more efficacious and thus more economic process. In addition, the utilisation of fluorinated intermediates of catharanthine according to the invention, for example: 20-fluoro-catharanthine 23 and 20,20-difluoro-3-hydro-4-hydroxycatharanthine 20, in coupling reactions with vindoline 3, permits preparation of novel dimeric alkaloids having potential anti-cancer activities. Other specific structural analogues of vinorelbine and vinflunine are easily accessed by this method.

All the preparation methods and reaction diagrams described hereinabove have been detailed in the case of preparation of fluorinated derivatives of catharanthine responding to the general formula (I) in which n=2. All the corresponding derivatives responding to the general formula (I) in which n=1 can be easily obtained by a process of ring contraction of the northern, catharanthine derived, portion of the dimers, by techniques familiar to the specialist and in particular those described by Andriamialisoa, R. Z.; Langlois, N.; Langlois Y.; Potier P. Tetrahedron, 1980, 36, 3053-3060.

The present invention will now be described in greater detail by means of the preparation examples mentioned hereinbelow by way of illustration of the principal stages resulting in the fluorinated derivatives of catharanthine, and in particular in 20,20-difluorocatharanthine.

Isocatharanthine (10)

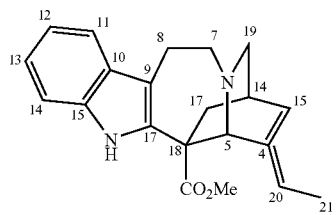

To a suspension of palladium (10% in mass) on carbon (5.7 g, 5.4 mmol, 0.2 equiv.) previously activated by hydrogen in MeOH (150 mL) is added (+)-catharanthine 2 (9.0 g, 26.8 mmol, 1 equiv.) in solution in MeOH (100 mL). The reaction mixture is placed under reduced pressure in hydrogen (0.3 bar), then isolated and left under reduced stirring at ambient temperature. The reaction is followed by $^1$H NMR until the starting product disappears (around 2 h). The reaction mixture is then filtered on celite 545, then recrystallised in MeOH to give the compound 10 (6.5 g, 19.3 mmol, 72%) in the form of translucent crystals.

Chemical formula: $C_{21}H_{24}N_2O_2$ M=336 g·mol$^{-1}$
Rf=0.35 (Hexane/AcOEt 3/7)
F=78° C.-81° C.
$^1$H NMR (CDCl$_3$): 8.08 (sl, 1H, NH); 7.53 (d, J=7.3 Hz, 1H, H-11); 7.26 (d, J=7.3 Hz, 1H, H-14); 7.22-7.10 (m, 2H, H-12 and H-13); 5.48-5.32 (m, 1H, H-20); 4.05 (s, 1H, H-5); 3.73 (s, 3H, CO$_2$CH$_3$); 3.62-3.46 (m, 1H, H-7); 3.44-3.24 (m, 2H, H-7 and H-8); 3.18-3.10 (m, 1H, H-19); 3.08-2.92 (m, 2H, H-19 and H-8); 2.88-2.74 (m, 1H, H-1); 2.44-2.26 (m, 2H, H-3); 2.20-2.08 (m, 1H, H-2); 1.90-1.78 (m, 1H, H-1); 1.62 (d, J=6.7 Hz, 3H, H-21).
$^{13}$C NMR (CDCl$_3$): 175.2; 137.7; 135.9; 129.5; 122.6; 120.1; 119.4; 119.0; 111.2; 111.1; 64.2; 56.1; 53.8; 53.3; 51.1; 38.0; 30.3; 27.9; 22.0; 13.4.
IR (film): 3368, 2916, 2855, 1714, 1461, 1264, 740 cm$^{-1}$.
MS (ESI TOF): 337 [M+H$^+$] (100).
$[\alpha]_D^{20}$=+35 (c=2.3; CHCl$_3$)

N$_a$-carbomethoxyisocatharanthine (11)

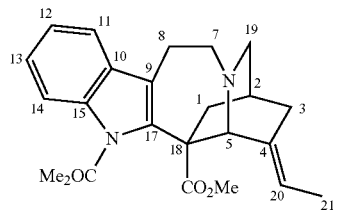

To a suspension of potassium hydride (0.72 g, 6.3 mmol, 1.5 equiv.) in THF (10 mL) at 0° C. is added dropwise a solution of 10 (1.35 g, 4 mmol, 1 equiv.) in THF (20 mL). After 30 minutes under stirring at 0° C., methyl chloroformate (0.5 mL, 6.3 mmol, 1.5 equiv.) is added dropwise. After 1 h under stirring at 0° C., the reaction medium is brought to ambient temperature and agitation is maintained for 18 h. An aqueous solution of saturated $K_2CO_3$ (10 mL) is added. The aqueous phase is extracted with $CH_2Cl_2$ (3×20 mL), the organic phases are collected, dried on $Na_2SO_4$ and concentrated under vacuum. The crude product is then purified by chromatography on silica (Eluent: $CH_2Cl_2$/MeOH 97/3) to give 11 (1.3 g, 3.3 mmol, 82%) in the form of a white solid.

Chemical formula: $C_{23}H_{26}N_2O_4$ M=394 g·mol$^{-1}$
Rf=0.4 ($CH_2Cl_2$/MeOH 94/6)
F=62° C.-64° C.
$^1$H NMR (CDCl$_3$): 8.08 (d, J=7.9 Hz, 1H, H-11); 7.48 (d, J=7.3 Hz, 1H, H-14); 7.38-7.16 (m, 2H, H-12 and H-13); 5.32-5.18 (m, 1H, H-20); 4.06 (s, 1H, H-5); 3.86 (s, 3H, $CO_2CH_3$); 3.68 (m, 1H, H-7); 3.54 (s, 3H, $CO_2CH_3$); 3.40-3.12 (m, 2H, H-7 and H-8); 2.99 (m, 1H, H-19); 2.86 (m, 1H, H-19); 2.80-2.65 (m, 2H, H-8 and H-1); 2.44 (d, J=16 Hz, 1H, H-3); 2.30 (d, J=16 Hz, 1H, H-3); 2.06 (m, 1H, H-2); 1.76 (d, J=14 Hz, 1H, H-1); 1.56 (d, J=6.7 Hz, 3H, H-21).
$^{13}$C NMR (CDCl$_3$): 173.4; 151.8; 138.1; 135.8; 129.5; 124.6; 122.7; 119.7; 118.2; 115.5; 60.6; 57.9; 54.1; 53.0; 52.0; 37.5; 29.7; 27.9; 21.8; 12.6.
MS (ESI TOF): 395 [M+H$^+$] (100).
HRMS (TOF MS ES+):
Value calculated for $C_{23}H_{27}N_2O_4$ 395.1971
Value found 395.1956
$[\alpha]_D^{20}$=+48 (c=1.0; CHCl$_3$)

N$_a$-carbomethoxy-19-oxoisocatharanthine (12)

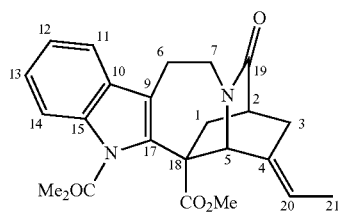

To 5 mL of an aqueous solution of $Na_2CO_3$ (675 mg, 6.4 mmol, 9.3 equiv.) is added a solution of 11 (270 mg, 0.69 mmol, 1 equiv.) in THF (10 mL). Iodine (800 mg, 3.2 mmol, 4.6 equiv.) in solution in THF (12 mL) is added dropwise at 0° C. The reaction mixture is then brought to ambient temperature and stirred for 18 hours. Next an aqueous solution saturated in $Na_2S_2O_3$ (15 mL) is added and the reaction mixture is left under stirring for 30 minutes. The aqueous phase is then extracted with $CH_2Cl_2$ (3×20 mL). The organic phases are combined, dried on $Na_2SO_4$ and concentrated under vacuum. The crude product is then purified by chromatography on silica (Eluent: $CH_2Cl_2$/MeOH 98/2) to give 12 (230 mg, 0.56 mmol, 82%) in the form of a white solid.

Chemical formula: $C_{23}H_{24}N_2O_5$ M=408 g·mol$^{-1}$
Rf=0.4 ($CH_2Cl_2$/MeOH 94/6)
F=94° C.-96° C.
$^1$H NMR (CDCl$_3$): 8.04-7.97 (m, 1H, H-11); 7.52-7.43 (m, 1H, H-14); 7.36-7.21 (m, 2H, H-12 and H-13); 5.53-5.41 (m, 1H, H-20); 4.66 (s, 1H, H-5); 4.32-4.17 (m, 1H, H-7); 3.93 (s, 3H, $CO_2CH_3$); 3.60 (s, 3H, $CO_2CH_3$); 3.28-3.15 (m, 3H, H-7 and H-8); 2.97 (dd, J=14 Hz and J=1.8 Hz, 1H, H-1); 2.84-2.76 (m, 1H, H-2); 2.56-2.48 (m, 2H, H-3); 2.00-1.89 (m, 1H, H-1); 1.59 (d, J=6.7 Hz, 3H, H-21).
$^{13}$C NMR (CDCl$_3$): 174.6; 172.0; 151.6; 136.4; 135.1; 132.5; 129.2; 124.9; 122.8; 120.9; 118.1; 117.0; 115.6; 61.5; 60.1; 58.7; 53.2; 52.1; 40.3; 38.9; 37.2; 28.5; 21.2; 20.8; 13.9; 13.1.
MS (ESI TOF): 409 [M+H$^+$] (100); 817 [2M+H$^+$] (34).
$[\alpha]_D^{20}$=+255 (c=0.4; CHCl$_3$)

(4R,20R)-N$_a$-carbomethoxy-3-hydro-4,20-dihydroxy-19-oxocatharanthine (13)

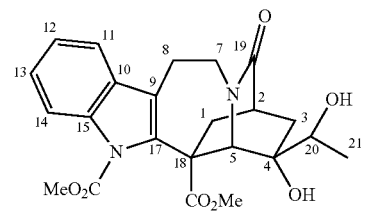

To a solution of 12 (1.26 g, 3.08 mmol, 1 equiv.) in an acetone/water mixture (8/1) (27 mL) at 0° C. are added $OsO_4$ in solution in t-BuOH (2.5%, 1.9 mL, 0.154 mmol, 0.05 equiv.), then by portion at 15 minutes NMO (0.72 g, 6.2 mmol, 2 equiv.). After 15 minutes at 0° C., the reaction mixture is left under stirring at ambient temperature for 18 h. The reaction is stopped by adding a saturated aqueous solution of $Na_2S_2O_3$ (15 mL) and water (15 mL) and left under stirring for 20 minutes. The reaction mixture is extracted with $CH_2Cl_2$ (4×30 mL). The organic phases are combined, dried on $Na_2SO_4$ and concentrated under vacuum. The crude product is then purified by chromatography on silica (Eluent: $CH_2Cl_2$/MeOH 97/3) to give 13 (1.16 g, 2.61 mmol, 85%) in the form of a white solid.

Chemical formula: $C_{23}H_{26}N_2O_7$ M=442 g·mol$^{-1}$
Rf=0.5 ($CH_2Cl_2$/MeOH 9/1)
F=102° C.-104° C.
$^1$H NMR (CDCl$_3$): 7.98 (d, J=7.9 Hz, 1H, H-11); 7.44 (d, J=7.9 Hz, 1H, H-14); 7.35-7.20 (m, 2H, H-12 and H-13); 4.77 (s, 1H, H-5); 4.30-4.18 (m, 1H, H-7); 4.05-3.93 (m, 1H, H-20); 3.92 (s, 3H, $CO_2CH_3$); 3.63 (s, 3H, $CO_2CH_3$); 3.34-3.08 (m, 3H, H-7 and H-8); 2.88 (dd, J=14.0 Hz J=1.8 Hz, 1H, H-1); 2.65-2.60 (m, 1H, H-2); 2.02-1.74 (m, 3H, H-1 and H-3); 1.16 (d, J=6.1 Hz, 3H, H-21).
$^{13}$C NMR (CDCl$_3$): 174.1; 172.5; 151.7; 135.3; 129.0; 125.1; 123.0; 118.2; 117.2; 115.6; 69.8; 59.2; 55.9; 53.4; 53.3; 52.9; 42.1; 38.5; 37.5; 36.7; 21.1; 17.8.
IR (tablet KBr): 3402, 2954, 1741, 1657, 1458, 760 cm$^{-1}$
MS (ESI TOF): 443 [M+H$^+$] (11); 465 [M+Na$^+$] (100); 907 [2M+Na$^+$] (36).
HRMS (TOF MS ES+):
Value calculated for $C_{23}H_{26}N_2O_7Na$ 465.1638
Value found 465.1631
$[\alpha]_D^{20}$=+97 (c=0.5; CHCl$_3$)

(4R,20R)-N$_a$-carbomethoxy-3-hydro-4,20-dihydroxysulphate-19-oxocatharanthine (14)

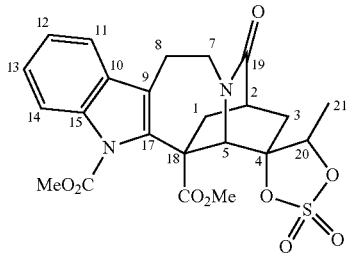

To a solution of diol 13 (200 mg, 0.45 mmol, 1 equiv.) in CH$_2$Cl$_2$ (5 mL) at 0° C. are added triethylamine (0.15 mL, 1.04 mmol, 2.3 equiv.) then, dropwise, thionyl chloride (43 μL, 0.59 mmol, 1.3 equiv.). After 30 min at 0° C., the reaction is stopped by adding a solution saturated in NaCl (5 mL) and water (5 mL). The aqueous phase is extracted with CH$_2$Cl$_2$ (3×10 mL). The organic phases are combined, dried on Na$_2$SO$_4$ and concentrated under vacuum.

The crude product is then placed directly into a mixture of 7.5 mL CH$_3$CN and 6.5 mL H$_2$O and is stirred vigorously. RuCl$_3$ (5 mg, 0.023 mmol, 0.05 equiv.) and NaIO$_4$ (242 mg, 1.13 mmol, 2.5 equiv.) are then added successively and after 1 h30 Et$_2$O (12 mL) is added. Agitation is prolonged for 10 min. The aqueous phase is extracted by 3×10 mL Et$_2$O then the combined organic phases are washed with water (30 mL), a solution saturated in NaHCO$_3$ (30 mL) and a solution saturated in NaCl (30 mL). The organic phase is then dried on Na$_2$SO$_4$ and concentrated under vacuum. Purification by chromatography on silica (eluent CH$_2$Cl$_2$/MeOH 98/2) results in 14 (137 mg, 0.27 mmol, 60%) in the form of a white solid.

Chemical formula: C$_{23}$H$_{24}$N$_2$O$_9$S M=504 g·mol$^{-1}$
Rf=0.5 (CH$_2$Cl$_2$/MeOH 95/5)
F=140° C.-142° C.
$^1$H NMR (CDCl$_3$): 7.98 (d, J=7.3 Hz, 1H, H-11); 7.44 (d, J=7.3 Hz, 1H, H-14); 7.37-7.30 (m, 2H, H-12 and H-13); 5.12 (s, 1H, H-5); 4.75 (q, J=6.7 Hz, 1H, H-20); 4.24-4.13 (m, 1H, H-5); 3.99 (s, 3H, CO$_2$CH$_3$); 3.68 (s, 3H, CO$_2$CH$_3$); 3.53-3.47 (m, 1H, H-7); 3.35-2.95 (m, 2H, H-8); 2.97 (dd, J=14.0 Hz and J=1.6 Hz, 1H, H-1); 2.90-2.85 (m, 1H, H-2); 2.45-2.38 (m, 2H, H-3); 2.02-1.96 (m, 1H, H-1); 1.64 (d, J=6.7 Hz, 3H, H-21).
$^{13}$C NMR (CDCl$_3$): 173.2; 171.5; 152.4; 136.1; 134.8; 129.3; 125.6; 123.5; 118.8; 117.5; 116.0; 94.8; 84.9; 56.9; 55.1; 54.0; 53.4; 40.9; 38.4; 37.7; 32.3; 21.2; 15.8.
IR (tablet KBr): 1735, 1687, 1459, 1382, 1215, 904 cm$^{-1}$.
MS (ESI TOF): 505 [M+H$^+$] (100); 1009 [M+Na$^+$] (13).
[α]$_D^{20}$=+165 (c=0.3; CHCl$_3$)

(20R)-N$_a$-carbomethoxy-20-hydroxy-19-oxocatharanthine (15)

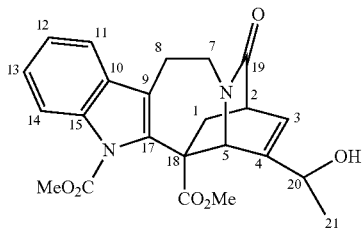

To a solution of sulphate 14 (1.59 g, 3.16 mmol, 1 equiv.) in THF (25 mL) is added dropwise a solution of NBu$_4$F (1M in THF, 6.3 mL, 6.3 mmol, 2 equiv.). After 18 h of stirring at ambient temperature, a solution of H$_2$SO$_4$ 2M in THF (37 mL) and 3.7 mL water are added. After 48 h of stirring at ambient temperature, a solution saturated in NaHCO$_3$ is added (200 mL). The aqueous phase is extracted with AcOEt (4×50 mL), the organic phases are combined, dried on Na$_2$SO$_4$, filtered then concentrated under vacuum. The crude product is then purified by chromatography on silica and 15 (828 mg, 1.95 mmol, 62%) is isolated in the form of a white solid.

Chemical formula: C$_{23}$H$_{24}$N$_2$O$_6$ M=424 g·mol$^{-1}$
Rf=0.3 (CH$_2$Cl$_2$/MeOH 95/5)
F=188° C.-190° C.
$^1$H NMR (CDCl$_3$): 7.98 (d, J=7.9 Hz, 1H, H-11); 7.44 (d, J=7.9 Hz, 1H, H-14); 7.35-7.20 (m, 2H, H-12 and H-13); 6.43 (d, J=6.3 Hz, 1H, H-3); 5.24 (d, J=1.7 Hz, 1H, H-5); 4.41-4.33 (m, 1H, H-20); 4.17-4.03 (m, 1H, H-7); 3.94 (s, 3H, CO$_2$CH$_3$); 3.57 (s, 3H, CO$_2$CH$_3$); 3.47-3.17 (m, 4H, H-8, H-2 and H-7); 2.88 (dd, J=14.0 Hz and J=1.8 Hz, 1H, H-1); 2.02 (dd, J=14.0 Hz and J=1.8 Hz, 1H, H-1); 1.33 (d, J=6.1 Hz, 3H, H-21).
$^{13}$C NMR (CDCl$_3$): 174.1; 173.8; 152.0; 145.3; 136.6; 135.3; 129.3; 128.5; 125.1; 123.1; 118.4; 116.7; 115.8; 67.1; 58.0; 54.3; 53.6; 52.8; 44.0; 40.7; 38.4; 21.3; 21.1.
IR (tablet KBr): 3414, 2944, 1743, 1653, 1458, 1437, 1327, 1242, 754 cm$^{-1}$.
MS (ESI TOF): 447 [M+Na$^+$] (100); 871 [2M+Na$^+$] (64).
[α]$_D^{20}$=+181 (c=0.7; CHCl$_3$)

N$_a$-carbomethoxy-19,20-dioxocatharanthine (16)

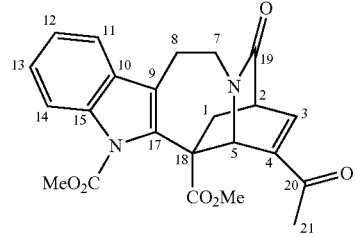

A solution of allylic alcohol 15 (100 mg, 0.236 mmol, 1 equiv.) in 8 mL of dichloromethane is cooled to 0° C. 140 mg of activated manganese dioxide (16 mmol, 70 equiv.) are added to this at once. The black suspension obtained is stirred at 0° C. for 1 h30 under nitrogen atmosphere then brought to ambient temperature.

The reaction mixture is filtered on celite 545 then washed thoroughly using dichloromethane. The filtrate is concentrated under reduced pressure to give the enone 16 (85 mg, 0.201 mmol, 85%) in the form of a white solid.

Chemical formula: C$_{23}$H$_{22}$N$_2$O$_6$ M=422 g·mol$^{-1}$
Rf=0.4 (EtOAc)
F=108° C.-110° C.
$^1$H NMR (CDCl$_3$): 8.01 (d, J=8.5 Hz, 1H, H-11); 7.49 (d, J=7.3 Hz, 1H, H-14); 7.45 (d, J=6.7 Hz, 1H, H-3); 7.37-7.23 (m, 2H, H-12 and H-13); 5.80 (d, J=1.8 Hz, 1H, H-5); 4.18-4.02 (m, 1H, H-7); 3.91 (s, 3H, CO$_2$CH$_3$); 3.65 (m, 1H, H-2); 3.49 (s, 3H, CO$_2$CH$_3$); 3.48-3.34 (m, 1H, H-8); 3.32-3.16 (m, 2H, H-7 and H-8); 2.82 (dd, J=12.8 Hz and J=2.4 Hz, 1H, H-1); 2.35 (s, 3H, H-21); 2.07 (dd, J=13.4 Hz and J=3.0 Hz, 1H, H-1).

$^{13}$C NMR (CDCl$_3$): 193.3; 172.2; 171.6; 151.9; 143.6; 142.3; 135.8; 135.3; 129.2; 125.2; 123.1; 118.4; 117.0; 115.8; 57.3; 53.5; 52.6; 52.5; 45.5; 41.3; 37.4; 24.6; 20.9.
IR (tablet KBr): 1740, 1668, 1252, 751 cm$^{-1}$.
MS (ESI TOF): 423 [M+H$^+$] (10); 445 [M+Na$^+$] (100); 867 [2M+Na$^+$] (32).
HRMS (TOF MS ES+):
Value calculated for C$_{23}$H$_{22}$N$_2$O$_6$Na 445.1376
Value found 445.1357
[α]$_D^{20}$+183 (c=1.8; CHCl$_3$)

20,20-difluoro-19-oxocatharanthine (17)

Fluorination: N$_a$ carbomethoxy
20,20-difluoro-19-oxocatharanthine

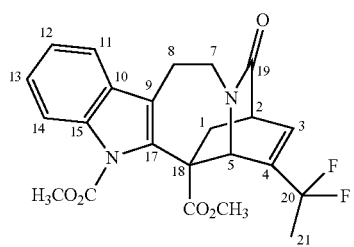

The enone 16 (300 mg, 0.71 mmol, 1 equiv.) is placed in solution in Deoxofluor™ (3 mL, 16.4 mmol, 23 equiv.). Three drops of ethanol are then added and the reaction mixture is left under stirring at 80° C. for 24 h. 0.6 mL of Deoxofluor™ (3.3 mmol, 5 equiv.) and two drops of ethanol are then added and agitation is continued at this temperature for a further 48 h (the reaction is followed by $^1$H NMR until the starting product disappears). The reaction medium is diluted in 200 mL of dichloromethane and 100 mL of an aqueous solution saturated in K$_2$CO$_3$ are then added. The mixture is left for 15 min under stirring at ambient temperature, then the aqueous phase is extracted by 3×50 mL of dichloromethane. The organic phases are combined, dried on Na$_2$SO$_4$ and concentrated under vacuum. The crude product is then purified by two filtrations on silica gel (CH$_2$Cl$_2$/MeOH 98/2 and C$_6$H$_{12}$/AcOEt 6/4) and the residue enters the following stage.
Chemical formula: C$_{23}$H$_{22}$N$_2$O$_5$F$_2$ M=444 g·mol$^{-1}$
Rf=0.3 (Hexane/AcOEt 40/60)
$^1$H NMR (CDCl$_3$): 8.01-7.99 (m, 1H, H-11); 7.53-7.47 (m, 1H, H-14); 7.38-7.28 (m, 2H, H-12 and H-13); 6.87-6.77 (m, 1H, H-3); 5.36 (d, J=1.8 Hz, 1H, H-5); 4.20-4.03 (m, 1H, H-7); 3.93 (s, 3H, CO$_2$CH$_3$); 3.61-3.54 (m, 1H, H-2); 3.57 (s, 3H, CO$_2$CH$_3$); 3.45-3.20 (m, 3H, H-8 and H-7); 2.93-2.83 (m, 1H, H-1); 2.09-1.98 (m, 1H, H-1); 1.81 (dd, J=18 Hz, J=18 Hz, 3H, H-21).

Deprotection of indole:
20,20-difluoro-19-oxocatharanthine (17)

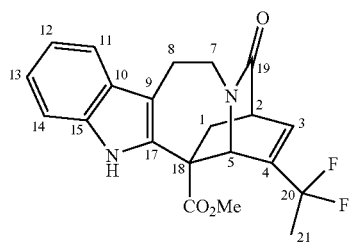

To a solution of the above protected 20,20-difluorocatharanthine in 100 mL of methanol are added in one time 2 g of potassium carbonate (14.5 mmol) and the suspension is stirred at ambient temperature for 18 h. 50 mL of water are then added to the now limpid reaction medium and the mixture is extracted by 3×50 mL dichloromethane. The combined organic phases are dried on Na$_2$SO$_4$ and concentrated under reduced pressure. The residue obtained is precipitated in a cyclohexane/ethyl acetate mixture 7/3 to give 17 (118 mg, 0.307 mmol, 43% in two steps) in the form of a white solid.
Chemical formula: C$_{21}$H$_{20}$F$_2$N$_2$O$_3$ M=386 g·mol$^{-1}$
Rf=0.3 (CH$_2$Cl$_2$/MeOH 95/5)
$^1$H NMR (CDCl$_3$): 7.95 (s, 1H, NH); 7.52 (d, J=Hz, 1H, H-11); 7.26 (d, J=Hz, 1H, H-14); 7.16-7.11 (m, 2H, H-12 and H-13); 6.83 (m, 1H, H-3); 5.55 (d, J=1 Hz, 1H, H-5); 4.24 (m, 1H, H-7); 3.67 (s, 3H, CO$_2$CH$_3$); 3.58 (m, 1H, H-2); 3.36-3.24 (m, 3H, H-8 and H-7); 2.82 (dd, J=13 Hz, J=2 Hz, 1H, H-1); 2.27 (dd, J=13 Hz, J=2 Hz, 1H, H-1); 1.82 (dd, J=18 Hz, J=18 Hz, 3H, H-21).
$^{13}$C NMR (CDCl$_3$): 172.8; 171.6; 139.5 (t, J=30 Hz); 135.8; 135.2 (t, J=9 Hz); 133.8; 127.7; 122.4; 119.7; 119.1 (t, J=233 Hz); 118.4; 110.6; 108.8; 56.3; 53.6; 53.0; 44.0; 42.8; 35.6; 22.4 (t, J=28 Hz); 20.7.
[α]$_D^{20}$=+155 (c=0.4; CHCl$_3$).

20,20-difluorocatharanthine (6)

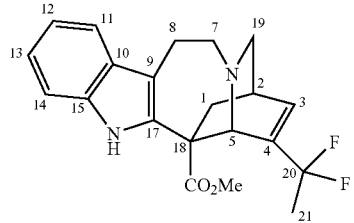

To a solution of 17 (140 mg, 0.36 mmol, 1 equiv.) in 50 mL of tetrahydrofurane are added in one time 360 mg of sodium borohydride (9.5 mmol, 26.5 equiv.). The resulting suspension is cooled to 0° C. and placed under stirring and nitrogen atmosphere. 1.9 mL (14.6 mmol, 40.5 equiv.) of trifuoroborane diethylic etherate are added dropwise, then the reaction mixture is brought to ambient temperature and stirred for 3 h. The solvent is evaporated under vacuum and replaced by 30 mL of methanol to which are added 6 mL of water and 4.5 mL of a solution of hydrochloric acid at 10%. The whole is stirred at ambient temperature for 15 h. The methanol is evaporated and replaced by 20 mL of dichloromethane. The medium is neutralised by addition of 40 mL of an aqueous solution saturated in sodium hydrogenocarbonate then extracted by 3×20 mL of dichloromethane. The combined organic phases, dried on Na$_2$SO$_4$, are concentrated under reduced pressure. Purification of the residue by chromatography on silica (eluent: CH$_2$Cl$_2$/MeOH 98/2) produces 74 mg (0.2 mmol, 55%) of 6 in the form of a white solid.
Chemical formula: C$_{21}$H$_{22}$F$_2$N$_2$O$_2$ M=372 g·mol$^{-1}$
Rf=0.5 (CH$_2$Cl$_2$/MeOH 95/5)
$^1$H NMR (CDCl$_3$): 7.68 (s, 1H, NH); 7.53 (d, J=7.5 Hz, 1H, H-11); 7.27 (d, J=7.5 Hz, 1H, H-14); 7.20 (td, J=7.5 Hz, J=1.5 Hz, 1H, H-13); 7.14 (td, J=7.5 Hz, J=1.5 Hz, 1H, H-12); 6.61 (m, 1H, H-3); 4.64 (d, J=2 Hz, 1H, H-5); 3.72 (s, 3H, CO$_2$CH$_3$); 3.63 (ddd, J=14 Hz, J=10 Hz, J=5 Hz, 1H, H-7); 3.43 (ddd, J=14 Hz, J=5 Hz, J=5 Hz, 1H, H-7); 3.32 (ddd, J=17 Hz, J=10 Hz, J=5 Hz, 1H, H-8); 3.01 (ddd, J=17 Hz, J=5 Hz, J=5 Hz, 1H, H-8); 2.88 (m, 3H, H-2 and H-19); 2.81 (dd, J=13 Hz, J=2 Hz, 1H, H-1); 1.84 (dd, J=18 Hz, J=18 Hz, 3H, H-21); 1.81 (d, J=13 Hz, 1H, H-1).

$^{13}$C NMR (CDCl$_3$): 173.4; 143.3 (t, J=28 Hz); 136.1; 135.3; 132.1 (t, J=9 Hz); 128.8; 122.1; 119.7 (t, J=232 Hz); 119.4; 118.3; 110.6; 110.4; 57.0; 55.3; 52.7; 52.3; 47.0; 37.0; 30.8; 22.6 (t, J=28 Hz); 21.6.

SM (ESI TOF): 353 [M−HF+H$^+$] (6); 373 [M+H$^+$] (100).

[α]$_D^{20}$=+43 (c=0.4; CHCl$_3$).

(4R)-N$_a$-carbomethoxy-3-hydro-4-hydroxy-19,20-dioxocatharanthine (18)

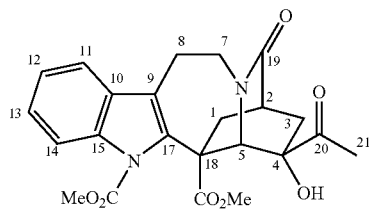

To a solution of oxalyl chloride (0.56 mL, 6.47 mmol, 2.2 equiv.) in CH$_2$Cl$_2$ (25 mL) maintained at −65° C. (internal temperature) is added dropwise DMSO (1.15 mL, 16.2 mmol, 5.5 equiv.) in solution in CH$_2$Cl$_2$ (0.850 mL). The mixture is stirred for 20 min, then a solution of diol 13 (1.3 g, 2.94 mmol, 1 equiv.) in CH$_2$Cl$_2$ (25 mL) is added dropwise as the temperature is regulated between −60° C. and −65° C. After 45 min of stirring, triethylamine (3.7 mL, 26.5 mmol, 9.0 equiv.) is added, then the temperature of the mixture is brought to ambient temperature over a period of 45 min. Water (20 mL) and brine (10 mL) are added, then the reaction mixture is extracted with CH$_2$Cl$_2$ (3×50 mL). The organic phases are combined, dried on Na$_2$SO$_4$ and concentrated under vacuum. The crude product is then purified by flash chromatography on silica (Eluent: CH$_2$Cl$_2$/MeOH 97/3) to give keto-alcohol 18 (647 mg, 1.47 mmol, 50%) in the form of a white solid and 13 (520 mg, 1.17 mmol, 40%).

Chemical formula: C$_{23}$H$_{24}$N$_2$O$_7$ M=440 g·mol$^{-1}$

F=123° C.-125° C.

Rf=0.2 (AcOEt)

$^1$H NMR (CDCl$_3$): 7.97 (d, J=8.5 Hz, 1H, H-11); 7.44 (d, J=7.3 Hz, 1H, H-14); 7.35-7.20 (m, 2H, H-12 and H-13); 5.16 (sl, 1H, OH); 5.04 (s, 1H, H-5); 4.23-4.04 (m, 1H, H-7); 3.91 (s, 3H, CO$_2$CH$_3$); 3.48 (s, 3H, CO$_2$CH$_3$); 3.41-3.35 (m, 2H, H-7 and H-8); 3.35-3.11 (m, 1H, H-8); 2.85 (dd, J=14.0 Hz and J=1.8 Hz, 1H, H-1); 2.79-2.71 (m, 1H, H-2); 2.59 (d, J=14.0 Hz, 1H, H-3); 2.25 (s, 3H, H-21); 2.26-2.15 (m, 1H, H-3); 1.91-1.79 (m, 1H, H-1).

$^{13}$C NMR (CDCl$_3$): 204.5; 174.3; 173.0; 151.9; 137.1; 135.0; 129.3; 125.1; 123.1; 118.4; 116.6; 115.8; 57.6; 54.9; 53.5; 52.7; 42.1; 38.9; 38.6; 34.9; 24.7; 21.2.

IR (tablet KBr): 3270, 2953, 1732, 1652, 1461, 759.747 cm$^{-1}$.

MS (ESI TOF): 441 [M+H$^+$] (100).

HRMS (TOF MS ES+):

Value calculated for C$_{23}$H$_{24}$N$_2$O$_7$Na 463.1481

Value found 463.1472

[α]$_D^{20}$=+121 (c=0.4; CHCl$_3$)

(4R)-N$_a$-carbomethoxy-20,20-difluoro-3-hydro-4-hydroxy-19-oxocatharanthine (19)

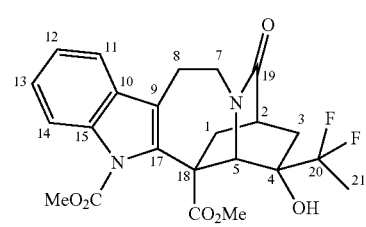

To a solution of keto-alcohol 18 (44 mg, 0.1 mmol, 1 equiv.) in CH$_2$Cl$_2$ (1 mL) at −78° C. is added DAST (67 μL, 0.5 mmol, 5 eq). The reaction mixture is then left under stirring at ambient temperature for 18 h. Next, an aqueous solution of NaHCO$_3$ at 10% (5 mL) is added dropwise at 0° C., the mixture is left for 15 min under stirring at ambient temperature, then the aqueous phase is extracted with CH$_2$Cl$_2$ (3×10 mL). The organic phases are combined, dried on Na$_2$SO$_4$ and concentrated under vacuum. The crude product is then purified by chromatography on silica (Eluent: Hexane/AcOEt 6/4) to give 19 (26 mg, 0.056 mmol, 56%).

Chemical formula: C$_{22}$H$_{24}$F$_2$N$_2$O$_6$ M=462 g·mol$^{-1}$

Rf=0.3 (EtOAc)

$^1$H NMR (CDCl$_3$): 7.98 (d, J=8.5 Hz, 1H, H-11); 7.49 (d, J=7.3 Hz, 1H, H-14); 7.36-7.26 (m, 2H, H-12 and H-13); 5.74 (s, 1H, H-5); 4.21-4.05 (m, 1H, H-7); 3.97 (s, 3H, CO$_2$CH$_3$); 3.66 (s, 3H, CO$_2$CH$_3$); 3.30-3.15 (m, 4H, H-8, H-7 and H-1); 2.73 (m, 1H, H-2); 2.62-2.52 (m, 1H, H-1); 2.15-2.05 (m, 1H, H-3); 1.83 (d, J=14 Hz, 1H, H-1); 1.66 (dd, J=19 Hz, J=19 Hz, 3H, H-21).

MS (ESI TOF): 485 [M+Na$^+$] (100).

N$_a$-carbomethoxy-20-fluoro-19-oxocatharanthine (22)

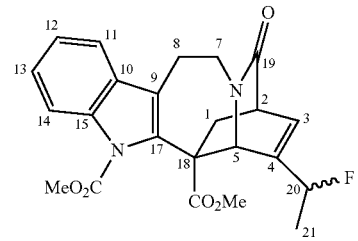

To a solution of DAST (8 μL, 0.06 mmol, 1.2 equiv.) in CH$_2$Cl$_2$ (0.1 mL) is added allylic alcohol 15 (20 mg, 0.05 mmol, 1 equiv.) in CH$_2$Cl$_2$ (0.7 mL). The reaction mixture is then left under stirring at ambient temperature for 15 min. Next, a saturated aqueous solution of K$_2$CO$_3$ (2 mL) is added dropwise at 0° C., the mixture is left for 15 min under stirring at ambient temperature, then the aqueous phase is extracted with CH$_2$Cl$_2$ (3×2 mL). The organic phases are combined, dried on Na$_2$SO$_4$ and concentrated under vacuum. The crude product is then purified on a preparative silica plate (eluent CH$_2$Cl$_2$/MeOH 98/2) to give 22 (10 mg, 0.023 mmol, 49%) in the form of two epimers A and B (white solid).

Chemical formula: C$_{23}$H$_{23}$FN$_2$O$_5$ M=426 g·mol$^{-1}$

Rf=0.4 (CH$_2$Cl$_2$/MeOH 95/5)

¹H NMR (CDCl₃): 8.02 (d, J=7.9 Hz, 1H, H-11); 7.49 (d, J=7.3 Hz, 1H, H-14); 7.35-7.20 (m, 2H, H-12 and H-13); 6.53-6.48 (m, 1H, H-3); 5.26 (d, J=1.8 Hz, 1H A, H-5); 5.22 (d, J=1.8 Hz, 1H B, H-5); 4.98 (dq, J=47.6 Hz and J=6.1 Hz, 1H, H-20); 4.20-4.04 (m, 1H, H-7); 3.93 (s, 3H, CO₂CH₃); 3.59 (s, 3H, CO₂CH₃); 3.53-3.48 (m, 1H, H-7); 3.43-3.19 (m, 3H, H-8 and H-2); 2.89-2.77 (m, 1H, H-1); 1.90 (d, J=13.4 Hz, 1H, H-1); 1.51 (dd, J=23.8 Hz, J=6.7 Hz, 1H A, H-21); 1.46 (dd, J=23.8 Hz, J=6.7 Hz, 1H B, H-21).

¹³C NMR (CDCl₃): 173.5; 171.8; 171.6; 151.9; 142.1; 141.9; 136.5; 136.4; 135.3; 130.0; 129.3; 125.1; 123.1; 118.3; 116.8; 115.8; 87.7 (d, J=161 Hz); 87.6 (d, J=161 Hz); 57.9; 57.7; 55.2; 54.7; 53.4; 53.3; 52.6; 44.3; 41.1; 40.9; 40.6; 38.7; 37.4; 29.6; 21.5; 21.1; 19.1 (d, J=23 Hz); 18.4 (d, J=23 Hz).

MS (ESI TOF): 465 [M+K⁺] (100), 891 [2M+K⁺] (33).

$N_a$-carbomethoxycatharanthine (26)

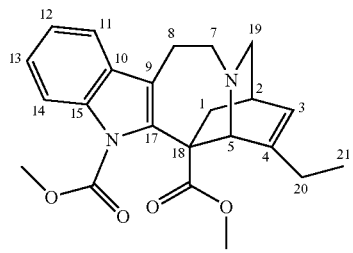

A solution of (+)-catharanthine 2 (1.0 g, 3.0 mmol, 1 equiv.) in THF (6 mL) is added dropwise to a suspension of potassium hydride at 0° C. (510 mg, 4.5 mmol, 1.5 equiv.) in THF (5 mL). After 1 h under stirring at 0° C., methyl chloroformate (0.35 mL, 4.5 mmol, 1.5 equiv.) is added dropwise. After 30 minutes under stirring at 0° C., an aqueous solution of saturated K₂CO₃ (10 mL) is added. The aqueous phase is extracted with CH₂Cl₂ (3×10 mL), the organic phases are collected, dried on Na₂SO₄, filtered and concentrated under vacuum. The crude product is then purified by chromatography on silica (Eluent: CH₂Cl₂/MeOH 97/3) to give 26 (280 mg, 2.1 mmol, 70%) in the form of a white solid.

Chemical formula: C₂₃H₂₆N₂O₄ M=394 g·mol⁻¹

¹H NMR (CDCl₃): 8.10 (d, J=7.3 Hz, 1H, H-11); 7.49 (d, J=7.3 Hz, 1H, H-14); 7.33-7.24 (m, 2H, H-12 and H-13); 5.99 (m, 1H, H-3); 4.21 (s, 1H, H-5); 3.87 (s, 3H, CO₂CH₃); 3.65 (m, 1H, H-7); 3.54 (s, 3H, CO₂CH₃); 3.23 (m, 1H, H-8); 3.03-2.85 (m, 3H, H-7 and H-19); 2.47 (m, 2H, H-2 and H-8); 2.48 (d, J=8.5 Hz, 1H, H-1); 2.24 (m, 1H, H-20); 1.91 (m, 1H, H-20); 1.71 (d, J=10.3 Hz, 1H, H-1); 1.08 (d, J=7.3 Hz, 3H, H-21).

¹³C NMR (CDCl₃): 172.9; 151.7; 147.3; 138.6; 135.9; 129.5; 124.5; 123.3; 122.7; 119.6; 118.2; 115.4; 58.5; 55.9; 55.8; 52.9; 52.7; 52.0; 38.2; 31.5; 26.7; 21.9; 10.3.

$N_a$-carbomethoxy-9-oxocatharanthine (27)

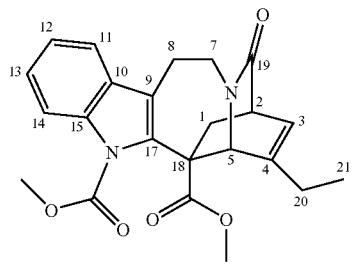

To 15 mL of an aqueous solution of Na₂CO₃ (2.07 g, 19.5 mmol, 9.3 equiv.) is added a solution of 26 (820 mg, 2.1 mmol, 1 equiv.) in THF (30 mL). Iodine (2.46 g, 9.7 mmol, 4.6 equiv.) in solution in THF (40 mL) is added dropwise at 0° C. The reaction mixture is then brought to ambient temperature and stirred for 18 hours. Next an aqueous solution saturated in Na₂S₂O₃ (30 mL) is added and the reaction mixture is left under stirring for 30 minutes. The aqueous phase is then extracted with CH₂Cl₂ (3×30 mL). The organic phases are combined, dried on Na₂SO₄, filtered and concentrated under vacuum. The crude product is then purified by chromatography on silica (Eluent: CH₂Cl₂/MeOH 98/2) to give 27 (787 mg, 1.93 mmol, 92%) in the form of a white solid.

Chemical formula: C₂₃H₂₄N₂O₅ M=408 g·mol⁻¹

¹H NMR (CDCl₃): 8.06-7.98 (m, 1H, H-11); 7.53-7.44 (m, 1H, H-14); 7.36-7.22 (m, 2H, H-12 and H-13); 6.23-6.17 (m, 1H, H-3); 4.84 (d, J=1.8 Hz, 1H, H-5); 4.19-4.03 (m, 1H, H-7); 3.92 (s, 3H, CO₂CH₃); 3.60 (s, 3H, CO₂CH₃); 3.47-3.37 (m, 1H, H-2); 3.36-3.15 (m, 3H, H-8 and H-7); 2.83-2.73 (m, 1H, H-1); 2.24-1.89 (m, 3H, H-20 and H-1); 1.08 (t, J=7.3 Hz, 3H, H-21).

¹³C NMR (CDCl₃): 174.5; 171.9; 151.8; 144.1; 136.8; 135.3; 129.3; 125.6; 125.0; 123.0; 118.2; 116.8; 115.7; 59.0; 57.7; 53.4; 52.4; 44.1; 41.0; 37.8; 26.5; 21.1; 11.0.

IR (film): 2996, 2959, 2881, 1739, 1681, 1461, 1443 cm⁻¹.

MS (IC): 409 [M+H⁺] (100).

$[\alpha]_D^{20}$=+141 (c=1.9; CHCl₃)

Allylic Oxidation of Protected Catharanthine (27) to Give (20R)-$N_a$-carbomethoxy-20-hydroxy-19-oxo-catharanthine (15)

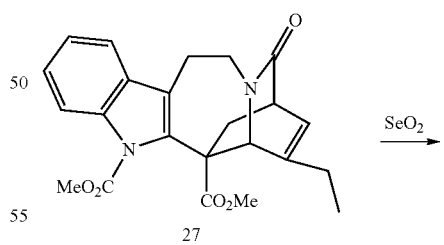

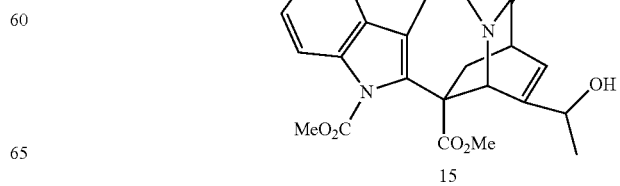

In a pressure tube of 25 mL, 50 mg of protected catharanthine 27 (0.123 mmol, 1 equiv.) is dissolved in 1.5 mL of ethanol 95%. 51 mg of selenium dioxide (0.459 mmol, 3.7 equiv.) in solution in 2.5 mL of ethanol 95% is added. The tube is hermetically sealed with a Teflon cork (equipped with a joint) and placed at 120° C. (temperature of the oil bath) under magnetic stirring. After 24 hours, 40 mg (0.36 mmol, 2.9 equiv.) of $SeO_2$ is added in one portion (in a solid form). This operation is repeated every 24 hours during 4 days (before every addition, the tube is brought at ambient temperature to be safely uncorked). After 5 days of reaction, the starting material is completely consumed. The reaction mixture is brought at ambient temperature and diluted with $Et_2O$. It is washed with 20 mL of brine. The aqueous phase is extracted with $Et_2O$ (3×20 mL). The organic phases are combined, dried on $Na_2SO_4$, filtered and concentrated under vacuum. The crude product is then purified by chromatography on silica (Eluent: $CH_2Cl_2$/MeOH 98/2 then 95/5) to give 35 mg (0.083 mmol, 67%) of a white solid corresponding to allylic alcohol 15, spectral characteristics of which are identical to those of the allylic alcohol obtained by the protocol using isocatharanthine.

Thus, 20,20-difluoro-catharanthine (6), (4R)-$N_a$-carbometoxy-20,20-difluoro-3-hydro-4-hydroxy-19-oxocatharanthine (19) after deprotections and $N_a$-carbometoxy-20-fluoro-19-oxocatharanthine (22) after deprotections, can be coupled, in a manner well known per se in the prior art, with vindoline, then subjected to a ring contraction reaction and if required to a reduction of the endocyclic double bond C3'-C4', so as to respectively result in vinflunine (1), 20',20'-difluorovinblastine (21) and 20'-fluorovinorelbine (25), which in turn can be subjected to an additional step of reduction of the double bond to result in the monofluorinated vinflunine analogue.

4',20'-Anhydrovinblastine (28)

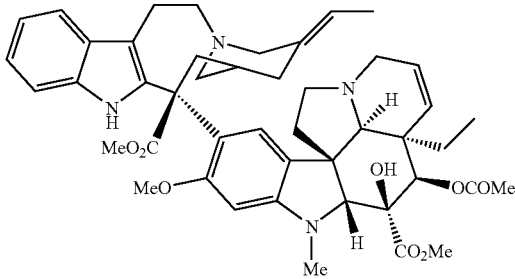

To a mixture of 60 mL of a glycine buffer and of 100 mL of a 0.1M hydrochloric acid aqueous solution is added in one time 1 g (2.98 mmol, 1 equiv.) of isocatharanthine 10. After complete dissolution, 1.36 g (1 equiv.) of vindoline, then 2.43 g (5 equiv.) of $FeCl_3$ are added. The reaction mixture, placed under nitrogen atmosphere, is stirred at ambient temperature for 15 h. The reaction is stopped by a dropwise addition of a solution of 172 mg (1.5 equiv.) of $NaBH_4$ in 15 mL of a 28% $NH_3$ aqueous solution. After 10 minutes of stirring at ambient temperature, 30 mL of $CH_2Cl_2$ and 30 mL of a solution of Rochelle salt are added and the mixture is vigorously stirred for 4 h. It is then extracted with $CH_2Cl_2$ (4×80 mL). The organic phases are combined, dried on $Na_2SO_4$, filtered and concentrated under vacuum. The crude product is then purified by chromatography on silica (Eluent: $CH_2Cl_2$/MeOH 95/5) to give 28 (1.18 g, 1.49 mmol, 50%).

Chemical formula: $C_{46}H_{56}N_4O_8$ M=792 g·mol$^{-1}$
$^1$H NMR (CDCl$_3$): 9.82 (sl, 1H); 7.99 (sl, 1H); 7.45 (d, J=7.6 Hz, 1H); 7.20-7.05 (m, 3H); 6.52 (s, 1H); 6.10 (s, 1H); 5.85 (dd, J=4 and 10 Hz, 1H); 5.57 (q, J=6.4 Hz, 1H); 5.43 (s, 1H); 5.28 (d, J=12 Hz, 1H); 3.81 (s, 3H); 3.78 (s, 3H); 3.76 (s, 1H); 3.61 (s, 3H); 3.60-3.08 (m, 10H); 2.91-2.79 (m, 2H); 2.72 (s, 3H); 2.65 (s, 1H); 2.45-2.31 (m, 3H); 2.16-2.05 (m, 5H); 1.84-1.71 (m, 2H); 1.67 (d, J=6.4 Hz, 3H); 1.35-1.29 (m, 1H); 1.24-1.18 (m, 1H); 0.78 (t, J=7.6 Hz, 3H).
$^{13}$C NMR (CDCl$_3$): 8.3; 12.8; 21.1; 24.6; 30.7; 31.8; 33.3; 34.7; 38.2; 42.6; 44.6; 47.5; 50.0; 50.2; 52.2; 52.4; 53.2; 55.2; 55.8; 56.9; 59.9; 65.2; 76.4; 79.7; 83.2; 94.0; 110.5; 116.8; 118.2; 119.0; 119.8; 120.6; 122.5; 122.7; 123.3; 124.6; 129.0; 129.9; 130.0; 133.1; 135.1; 152.8; 158.0; 170.9; 171.6; 174.6.
MS (ESI-TOF): 793 [M+H$^+$] (100).

nor-7'-4',20'-Anhydrovinblastine (29)

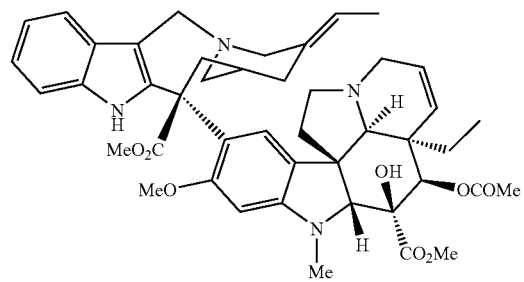

At 0° C., a solution of 30 µL (1 equiv.) of trifluoroacetic acid in 3 mL of $CH_2Cl_2$ is added dropwise to a solution of 296 mg (0.374 mmol, 2 equiv.) of 4',20'-anhydrovinblastine 28 diluted in 3 mL of anhydrous $CH_2Cl_2$. After 10 min of stirring, the mixture is cooled at −78° C. and 67 mg (1 equiv.) of NBS in solution in 3 mL of $CH_2Cl_2$ are added dropwise. After 20 min at −78° C., the cold bath is removed and after 15 min, 15 mL of a 10% aqueous solution of $K_2CO_3$ is added. The mixture is extracted with $CH_2Cl_2$ (3×15 mL). The organic phases are combined, dried on $Na_2SO_4$, filtered and concentrated under vacuum. The crude product is dissolved in 40 mL of a mixture THF/water 1/1 and 182 mg (2.5 equiv.) of silver tetrafluoroborate are added in one time. The mixture is brought at temperature ambient and 30 mL of a 10% aqueous solution of $Na_2CO_3$ are added. The mixture is extracted with $Et_2O$ (2×30 mL), then with $CH_2Cl_2$ (2×30 mL). The organic phases are combined, dried on $Na_2SO_4$, filtered and concentrated under vacuum Purification by chromatography on silica (Eluent: $CH_2Cl_2$/MeOH 93/7) give 29 (58 mg, 0.075 mmol, 20%) in the form of a beige solid.

Chemical formula: $C_{45}H_{54}N_4O_8$ M=778 g·mol$^{-1}$
$^1$H NMR (CDCl$_3$): 9.81 (s, 1H); 8.40 (s, 1H); 7.81 (d, J=8 Hz, 1H); 7.18-7.09 (m, 3H); 6.28 (s, 1H); 6.09 (s, 1H); 5.84 (dd, J=4 and 10.4 Hz, 1H); 5.74 (q, J=6.4 Hz, 1H); 5.38 (s, 1H); 5.26 (d, J=10.8 Hz, 1H); 4.55-4.45 (m, 2H); 3.86 (d, J=13.6 Hz, 1H); 3.82 (s, 3H); 3.77 (s, 3H); 3.71 (s, 1H); 3.68 (s, 3H); 3.50-3.21 (m, 5H); 2.81-2.71 (m, 6H); 2.63-2.45 (m, 4H); 2.12-2.05 (m, 4H); 1.83 (m, 12H); 1.77 (d, J=6.4 Hz, 3H); 1.91 (m, 1H); 1.41 (m, 1H); 1.23 (m, 1H); 0.69 (t, J=7.6 Hz, 3H).
$^{13}$C NMR (CDCl$_3$): 8.1; 13.0; 21.0; 30.0; 30.6; 32.4; 33.5; 38.1; 42.6; 44.5; 45.4; 47.5; 49.7; 50.2; 52.1; 52.7; 53.2; 55.0; 55.7; 59.8; 65.0; 76.3; 79.6; 83.0; 93.9; 110.4; 118.9; 119.8; 120.6; 122.2; 122.9; 123.3; 124.8; 128.4; 129.7; 133.5; 134.5; 152.9; 157.9; 170.8; 171.5; 174.0.
MS (ESI-TOF): 779 [M+H$^+$] (100).

The invention claimed is:

1. Fluorinated catharanthine derivatives responding to the general formula I:

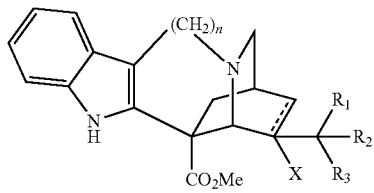

in which:
the dotted line expresses the possibility of the presence of a double bond when the substitution —X is absent or —X is a group selected from the group consisting of:
H,
OR,
NR'R",
SR, and
a halogen atom with R, R' and R" designate independently of one another a hydrogen atom or a linear or branched alkyl group in $C_1$ to $C_6$,
$R_1$, $R_2$ and $R_3$ represent independently of one another an atom of hydrogen, fluorine or a methylated group, on the condition all the same that at least one of the radicals $R_1$ and $R_2$ represents an atom of fluorine, and
n=1 or 2.

2. 20,20-Difluorocatharanthine as claimed in the formula of claim 1, in which the double bond in dotted lines is present, $R_1$ represents a methylated group, $R_2$, $R_3$ each represent an atom of fluorine, and n=2.

3. 20-Fluorocatharanthine as claimed in the formula of claim 1, in which the double bond in dotted lines is present, $R_1$, $R_2$ and $R_3$ represent respectively a hydrogen, a fluorine and a methylated group, and n=2.

4. 20,20-Difluoro-4-hydroxycatharanthine as claimed in the formula of claim 1, in which the bond in dotted lines is absent, —X represents the group —OH, $R_1$ is the methylated group, $R_2$, $R_3$ each represent an atom of fluorine, and n=2.

5. A process for preparing a fluorinated dimeric alkaloid of *Vinca*, which comprises forming a fluorinated derivative of catharanthine as claimed in claim 1 as a synthesis intermediate.

6. A process for preparing a fluorinated dimeric alkaloid of *Vinca*, which comprises a coupling reaction with a fluorinated derivative of catharanthine of claim 1 and with vindoline or with a derivative of vindoline.

7. The process as claimed in claim 6, wherein said fluorinated dimeric alkaloid of *Vinca* is vinflunine, which is prepared by coupling vindoline with 20,20-difluorocatharanthine, resulting in 20',20'-difluoro-3',4'-anhydrovinblastine.

8. The process as claimed in claim 7, wherein the 20',20'-difluoro-3',4'-anhydrovinblastine resulting from said coupling is subjected to a ring contraction reaction, followed by a reduction reaction of the endocyclic double bond at position $C_{3'}$-$C_{4'}$—.

9. A process for preparation of a fluorinated derivative of catharanthine as claimed in claim 1, which comprises oxidation of the lateral chain of catharanthine prior to a fluorination reaction.

10. The process as claimed in claim 9, wherein said oxidation is preceded by a stage of activation of the lateral chain by isomerisation of the endocyclic double bond to the exocyclic position by catalytic hydrogenation.

11. The process as claimed in claim 10, wherein said exocyclic double bond is subjected to a dihydroxylation reaction, after protection of the two nitrogen atoms, resulting in the formation of a diol.

12. The process as claimed in claim 11, wherein the diol obtained is activated in the form of a cyclic sulphate, transformed into allylic alcohol, then oxidised in the corresponding enone, which is subjected to a difluorination reaction, then deprotection of the indol and reduction of the amidic group to result in 20,20-difluorocatharanthine.

13. The process as claimed in claim 9, wherein it implies protection of the two nitrogen atoms of catharanthine, followed by allylic oxidation of the lateral chain of catharanthine in alcohol or in ketone prior to the fluorination reaction.

14. The process as claimed in claim 9, wherein the oxidation step is carried out in conditions leading to the formation of an oxidised catharanthine derivative of formula II:

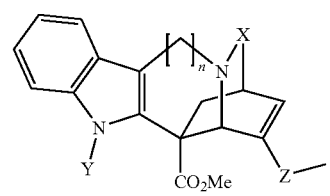

in which:
n=1 or 2,
X designates a C=O, or C=S group,
Y designates a $CO_2R$, $SO_2R$ or COR group with R designating an aryl group or a linear or branched alkyl group in $C_1$ to $C_4$ and
Z designates a CH—OH or C=O group.

15. Oxidised catharanthine derivative of formula II:

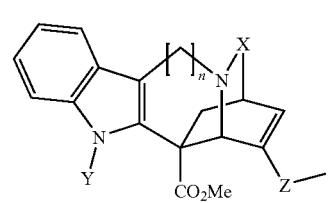

in which:
n=1 or 2,
X designates a C=O, or C=S group,
Y designates a $CO_2R$, $SO_2R$ or COR group with R designating an aryl group or a linear or branched alkyl group in $C_1$ to $C_4$ and
Z designates a CH—OH or C=O group.

16. Oxidised catharanthine derivative according to formula II as claimed in claim 15, in which—n=2, X designates a C=O group, Y designates a CO$_2$R group with R designating a linear or branched alkyl group in C$_1$ to C$_4$, Z designates a CH—OH or C=O group.

17. A process for preparing a fluorinated dimeric alkaloid of *Vinca*, which comprises forming an oxidised derivative of catharanthine as claimed in claim 15 as a synthesis intermediate.

18. A process for preparing a fluorinated dimeric alkaloid of *Vinca*, which comprises a fluorination reaction of the oxidised derivative of catharanthine of claim 15, followed by deprotection of the two nitrogen atoms.

19. The process as claimed in claim 18, wherein the preparation of the alkaloid dimeric further comprises a coupling reaction between the said fluorinated derivative of catharanthine, resulting from reactions of fluorination and deprotection, and vindoline or a derivative of vindoline.

20. The process as claimed in claim 17, wherein said fluorinated dimeric alkaloid of *Vinca* is vinflunine, which is prepared by coupling vindoline with 20,20-difluorocatharanthine, obtained by fluorination and deprotection of the two nitrogen atoms of the oxidised derivative of catharanthine as claimed in claim 16 for which Z=C=O, resulting in 20',20'-difluoro-3',4'-anhydrovinblastine.

21. The process as claimed in claim 20, wherein the 20',20'-difluoro-3',4'-anhydrovinblastine resulting from said coupling is subjected to a ring contraction reaction, followed by a reduction reaction of the endocyclic double bond at position C$_{3'}$-C$_{4'}$.

22. Isocatharanthine corresponding to the following formula (10):

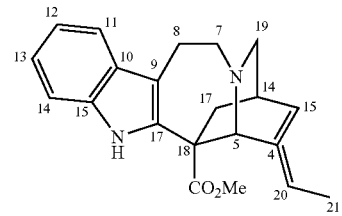

(10)

23. A process for preparing a fluorinated dimeric alkaloid of *Vinca*, which comprises forming isocatharanthine as a synthesis intermediate.

24. A process for preparing a fluorinated dimeric alkaloid of *Vinca*, which comprises a coupling reaction with isocatharanthine of claim 22 and with vindoline or with a derivative of vindoline.

25. The process as claimed in claim 24 wherein said fluorinated dimeric alkaloid of *Vinca* is vinflunine, which is prepared by coupling vindoline with isocatharanthine, resulting in 4',20'-anhydrovinblastine.

26. The process as claimed in claim 25, wherein 4',20'-anhydrovinblastine resulting from said coupling is subjected to a ring contraction reaction, followed by a gem-difluorination reaction, and wherein the order of these two steps is interchangeable.

* * * * *